(12) United States Patent
Lee et al.

(10) Patent No.: US 9,456,795 B2
(45) Date of Patent: Oct. 4, 2016

(54) X-RAY IMAGING APPARATUS AND CONTROL METHOD THEREOF

(71) Applicant: SAMSUNG ELECTRONICS CO., LTD., Suwon-si (KR)

(72) Inventors: Jong Ha Lee, Hwaseong-si (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 244 days.

(21) Appl. No.: 14/452,734

(22) Filed: Aug. 6, 2014

(65) Prior Publication Data

US 2015/0055746 A1 Feb. 26, 2015

(30) Foreign Application Priority Data

Aug. 21, 2013 (KR) ........................ 10-2013-0098969

(51) Int. Cl.
*A61B 6/04* (2006.01)
*A61B 6/00* (2006.01)

(52) U.S. Cl.
CPC ............. *A61B 6/467* (2013.01); *A61B 6/0414* (2013.01); *A61B 6/44* (2013.01); *A61B 6/502* (2013.01); *A61B 6/542* (2013.01); *A61B 6/545* (2013.01)

(58) Field of Classification Search
CPC ...... A61B 6/467; A61B 6/502; A61B 6/545; A61B 6/44; A61B 6/542; A61B 6/0414
USPC .......................................................... 378/37
See application file for complete search history.

(56) References Cited

U.S. PATENT DOCUMENTS

| | | | |
|---|---|---|---|
| 2004/0161075 A1* | 8/2004 | Amitani | A61B 6/0457 378/37 |
| 2006/0115041 A1* | 6/2006 | Roncaglioni | A61B 6/0414 378/37 |
| 2008/0181360 A1* | 7/2008 | Hemmendorff | A61B 6/502 378/37 |

* cited by examiner

*Primary Examiner* — Courtney Thomas
(74) *Attorney, Agent, or Firm* — Sughrue Mion, PLLC

(57) ABSTRACT

An X-ray imaging apparatus automatically distinguishes between right and left breasts during mammography. The X-ray imaging apparatus includes: an X-ray assembly configured to press a breast, irradiate X-rays onto the pressed breast, and detect X-rays transmitted through the breast; two handles respectively provided in both sides of the X-ray assembly so that a patient is able to grip the handles, each handle including a sensor for detecting the patient's grip; and a controller configured to determine a position of a handle including the sensor that has detected the patient's grip, and to determine that a breast subject to mammography is a breast corresponding to the determined position.

19 Claims, 20 Drawing Sheets

111

X-RAY IMAGING APPARATUS AND CONTROL METHOD THEREOF

CROSS-REFERENCE TO RELATED APPLICATION

This application claims priority from Korean Patent Application No. 10-2013-0098969, filed on Aug. 21, 2013 in the Korean Intellectual Property Office, the disclosure of which is incorporated herein by reference in its entirety.

BACKGROUND

1. Field

Apparatuses and methods consistent with exemplary embodiments relate to an X-ray imaging apparatus for obtaining an X-ray image by transmitting X-rays through an object, specifically, through breasts, and a control method thereof.

2. Description of the Related Art

An X-ray imaging apparatus acquires an image of an object by irradiating X-rays onto the object and detecting X-rays transmitted through the object. The X-ray imaging apparatus visualizes the inside structure of an object according to the intensities or strengths of X-rays transmitted through the object, based on a fact that X-rays show different transmission characteristics depending on the properties of materials constituting an object.

An X-ray imaging apparatus designed to acquire X-ray images of breasts has structural characteristics that are different from those of other X-ray imaging apparatuses, because mammography must be performed after a breast is flattened in order to acquire an X-ray image which accurately shows the inner structure of the breasts. In order to do so, a breast is positioned on the upper part of a bucky and pressed by the pressure paddle.

In mammography, generally, both a cranio-caudal view and a mediolateral oblique view of breasts are acquired. In the mediolateral oblique view, the left and right breasts can be distinguished by inclined directions of the breasts, but, in the cranio-caudal view, distinguishing between left and right breasts is difficult. Accordingly, an operator needs to input information indicating left and right breasts before mammography. In this case, the operator may input wrong information or may forget inputting information indicating left and right breasts, which may result in misdiagnosis or in taking additional X-ray images.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments provide an X-ray imaging apparatus for automatically distinguishing between left and right breasts using sensors.

In accordance with an exemplary embodiment, an X-ray imaging apparatus for mammography includes: an X-ray assembly configured to press a breast, to irradiate X-rays onto the pressed breast, and to detect X-rays transmitted through the breast; at least two handles provided in both sides of the X-ray assembly such that a patient is able to grip the handles, and respectively including at least one sensor for detecting the patient's grip; and a controller configured to determine, if one of the sensors detects the patient's grip, a position of a handle including the sensor that has detected the patient's grip, and to determine that a breast being subject to mammography is a breast corresponding to the determined position.

In accordance with an exemplary embodiment, an X-ray imaging apparatus for mammography includes: an X-ray source configured to irradiate X-rays onto a breast; an X-ray detector configured to detect X-rays transmitted through the breast; a pressure paddle configured to press a breast placed on the X-ray detector; at least two sensors installed in at least one of the X-ray detector and the pressure paddle, and configured to detect breasts placed close to the sensors; and a controller configured to determine, if one of the sensors detects a breast, that a breast being subject to mammography is an opposite breast of the breast detected by the corresponding sensor.

In accordance with an exemplary embodiment, an X-ray imaging apparatus for mammography includes: an X-ray assembly including an X-ray source configured to irradiate X-rays onto a breast, an X-ray detector configured to detect X-rays transmitted through the breast, and a pressure paddle configured to press a breast placed on the X-ray detector; at least two handles provided in both sides of the X-ray assembly such that a patient is able to grip the handles, and respectively including at least one first sensor for detecting the patient's grip; and at least two second sensors installed in at least one of the X-ray detector and the pressure paddle, and configured to detect breasts placed close to the second sensors; and a controller configured to determine whether a breast being subject to mammography is a left breast or a right breast, based on signals output from the first sensors and the second sensors.

Therefore, since a patient's left and right breasts can be automatically distinguished, an error that may be generated when an operator inputs information indicating left and right breasts may be prevented.

Also, by providing information about left and right breasts when an operator inputs information indicating the left and right breasts, possibility that the operator inputs wrong information may be lowered.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
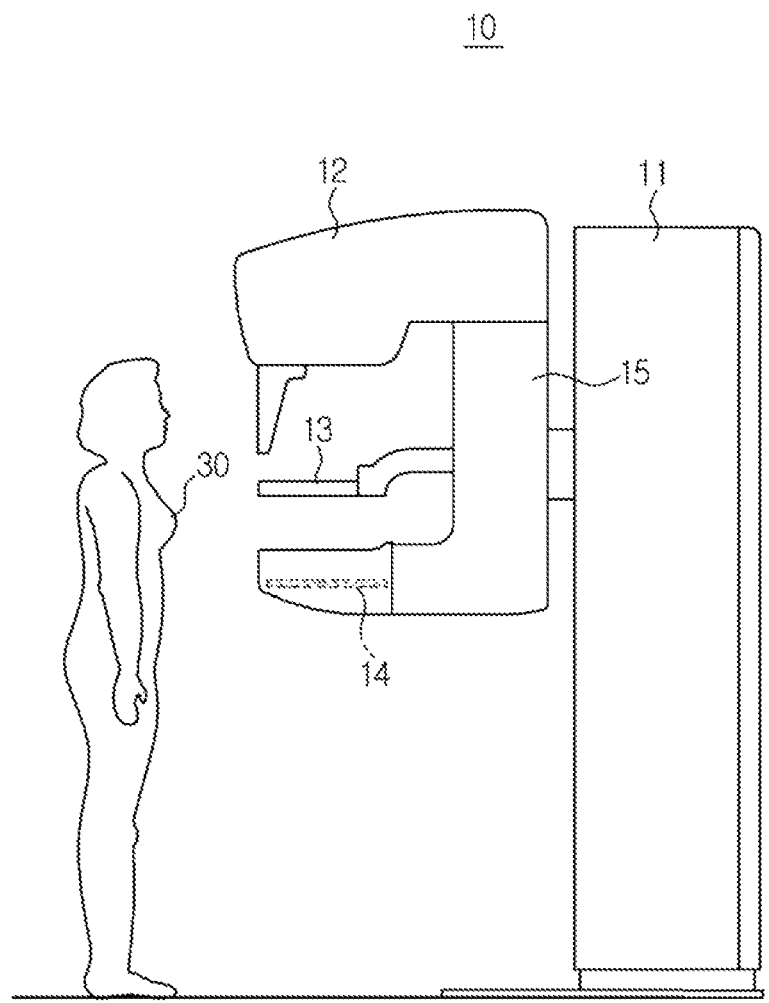
FIG. 1 illustrates an X-ray imaging apparatus for mammography according to an exemplary embodiment.

Certain exemplary embodiments are described in greater detail below with reference to the accompanying drawings. In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

FIG. 1 illustrates an X-ray imaging apparatus for mammography according to an exemplary embodiment.

An X-ray imaging apparatus 10 for mammography, among various kinds of X-ray imaging apparatuses, has a structure specialized to image breasts. As illustrated in FIG. 1, an X-ray source 12 and an X-ray detector 14 are connected to a main body 11, the X-ray source 12 irradiates X-rays onto a breast 30 placed between the X-ray source 12 and the X-ray detector 14, and the X-ray detector 14 detects X-rays transmitted through the breast 30 to acquire an X-ray image of the breast 30.

The X-ray imaging apparatus 10 further include a pressure paddle 13 located between the X-ray source 12 and the X-ray detector 14. The pressure paddle 13 presses the breast 30 placed on the X-ray detector 14. Operation of the pressure paddle 13 will be described in more detail with reference to FIGS. 2 and 3, below.

Figure 2:
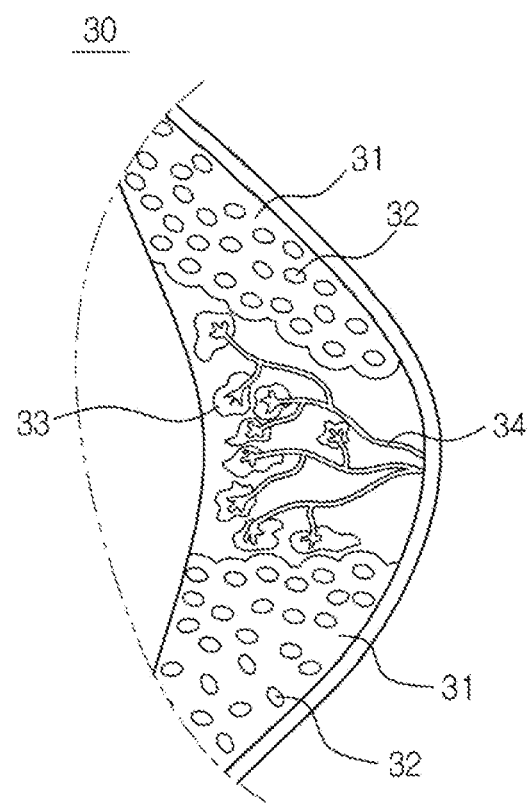
FIG. 2 illustrates an internal structure of a breast.
Figure 3:
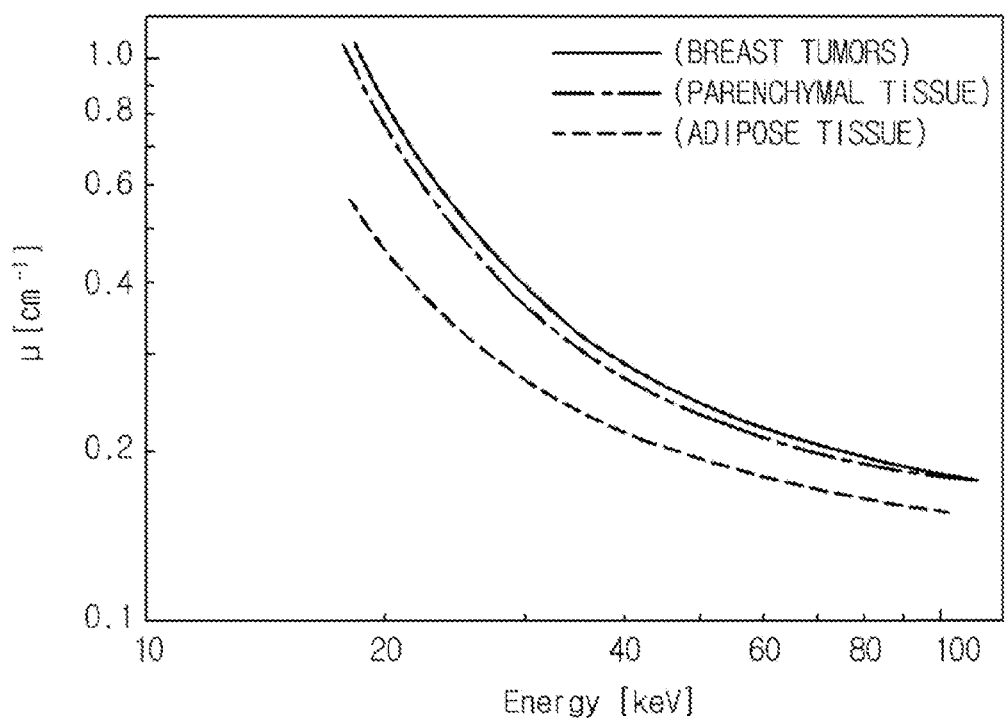
FIG. 3 is a graph showing relationships between energy bands and attenuation coefficients with respect to breast tumors, parenchymal tissue, and adipose tissue.

FIG. 2 illustrates an internal structure of a breast, and FIG. 3 is a graph showing attenuation coefficients with respect to inner materials of breasts.

Referring to FIG. 2, the inner tissue of a breast 30 includes a fibrous tissue 31 surrounding the breast 30 and maintaining the shape of the breast 30, adipose tissue 32 distributed over the whole area of the breast 30, grandular tissue 33 to make breast milk, duct tissue 34 that are transfer ducts of breast milk, etc. Tissue, such as the grandular tissue 33 and the duct tissue 34, participating in making and supplying breast milk among the above-mentioned tissue is called fibroglandular tissue.

An attenuation coefficient is data representing a degree at which X-rays attenuate when transmitting through an object, and the internal structure of an object can be visualized based on a fact that different inner materials of an object have different attenuation coefficients.

FIG. 3 is a graph showing relationships between energy bands and attenuation coefficients with respect to breast tumors, parenchymal tissue, and adipose tissue, which are inner materials of breasts. As shown in FIG. 3, attenuation coefficients of the inner materials of the breasts do not show great differences. The reason is because the breast 30 consists of only soft tissue as illustrated in FIG. 2. Accordingly, in order to acquire a clear X-ray image, it is needed to thin the thickness of the breast 30 by pressing the breast 30 with the pressure paddle 13 (see FIG. 1). If the thickness of the breast 30 is thinned, an amount of X-rays to which the breast 30 is exposed can also be reduced.

Referring again to FIG. 1, the pressure paddle 13 may be connected to a frame 15 connecting the X-ray source 12 to the X-ray detector 14 in such a manner to be movable in an up-down direction. When the breast 30 is placed on the X-ray detector 14 for mammography, the pressure paddle 13 presses the breast 30, and mammography is performed through irradiation and detection of X-rays while the breast 30 is maintained pressed.

Upon mammography, generally, both a cranio-caudal view and a mediolateral oblique view of breasts are acquired. In the mediolateral oblique view, the left and right breasts can be distinguished by inclined directions of the breasts, but, in the cranio-caudal view, distinguishing between the left and right breasts is difficult. Accordingly, an operator needs to input information indicating the left and right breasts before mammography, and in this case, the operator may input wrong information or may forget about inputting information indicating the left and right breasts.

In order to overcome the problem, an X-ray imaging apparatus according to an exemplary embodiment distinguishes between left and right breasts when a cranio-caudal view of the breasts is acquired. Hereinafter, the configuration and operations of the X-ray imaging apparatus will be described in detail.

Figure 4A:
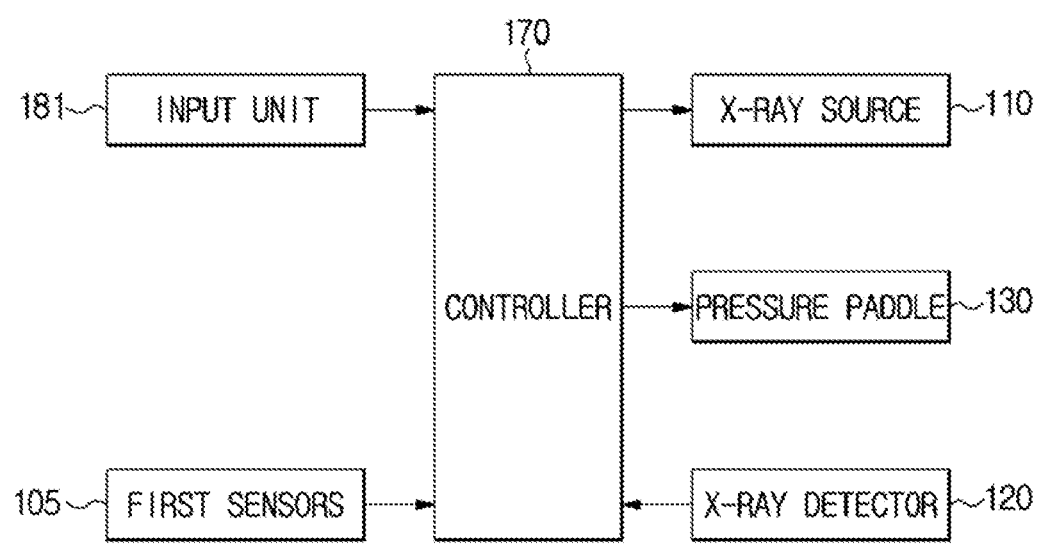
FIG. 4A is a block diagram of an X-ray imaging apparatus according to an exemplary embodiment.
Figure 4B:
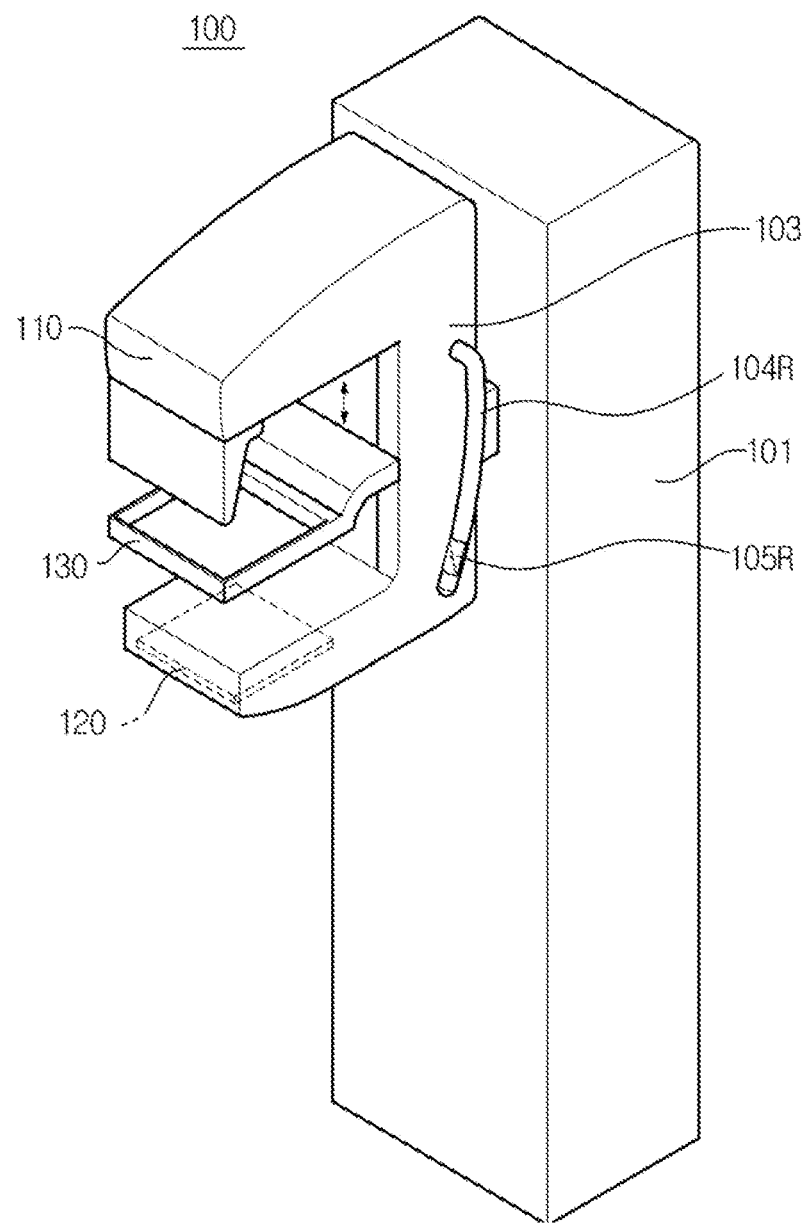
FIGS. 4B and 4C illustrate an X-ray imaging apparatus according to an exemplary embodiment when the X-ray imaging apparatus is seen from the right side and when the X-ray imaging apparatus is seen from the left side.
Figure 4C:
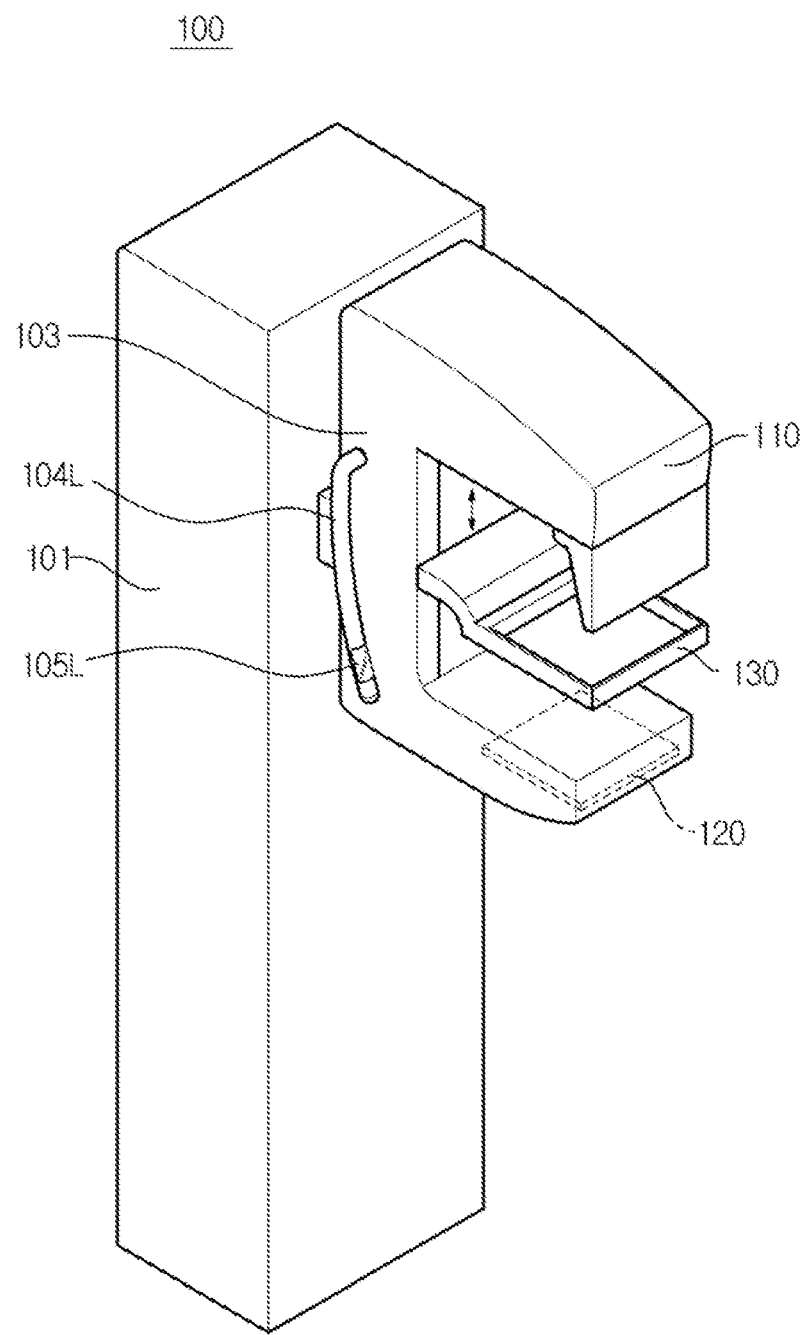
Figure 5A:
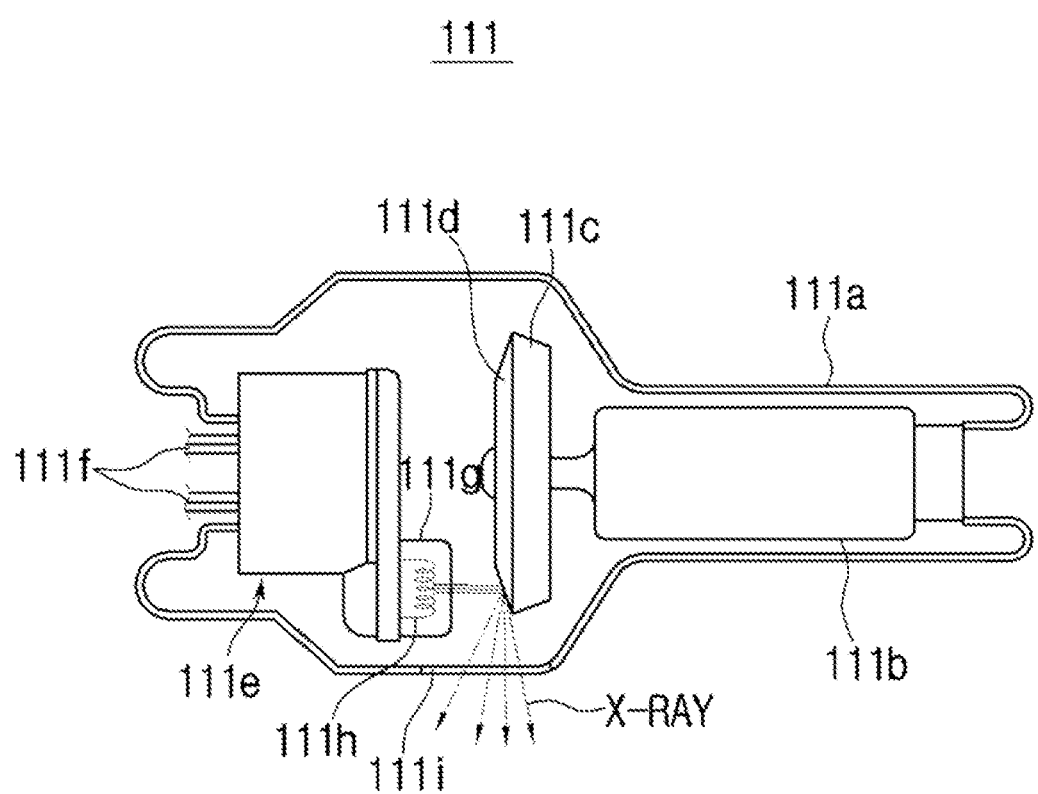
FIG. 5A illustrates an X-ray tube.
Figure 5B:
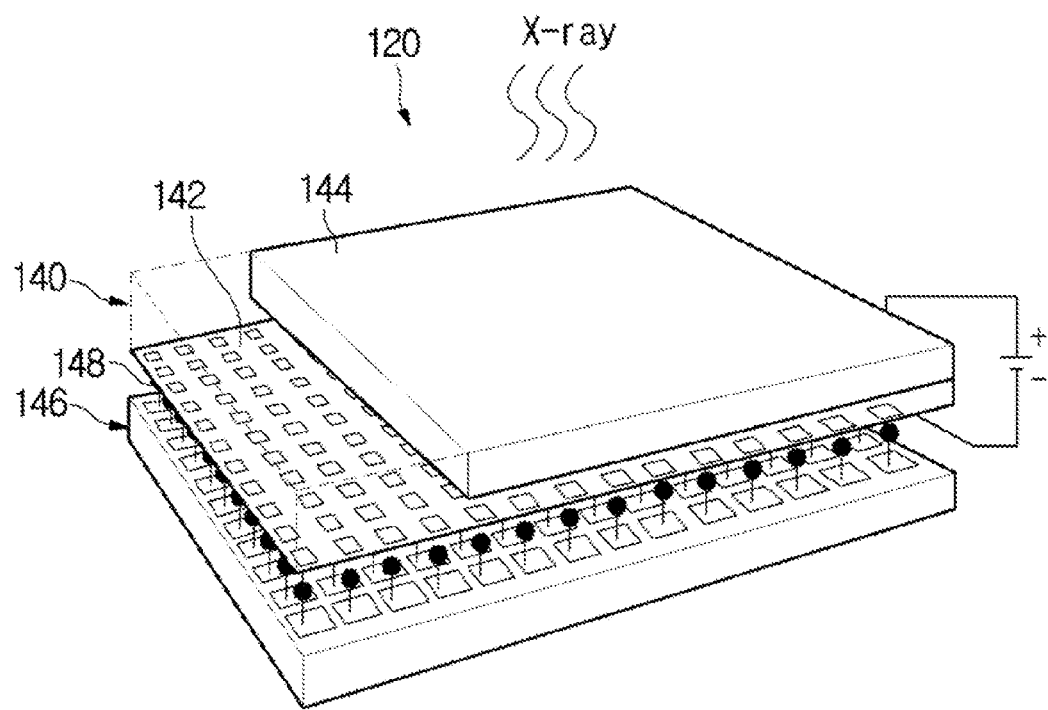
FIG. 5B illustrates a structure of an X-ray detector.
Figure 6A:
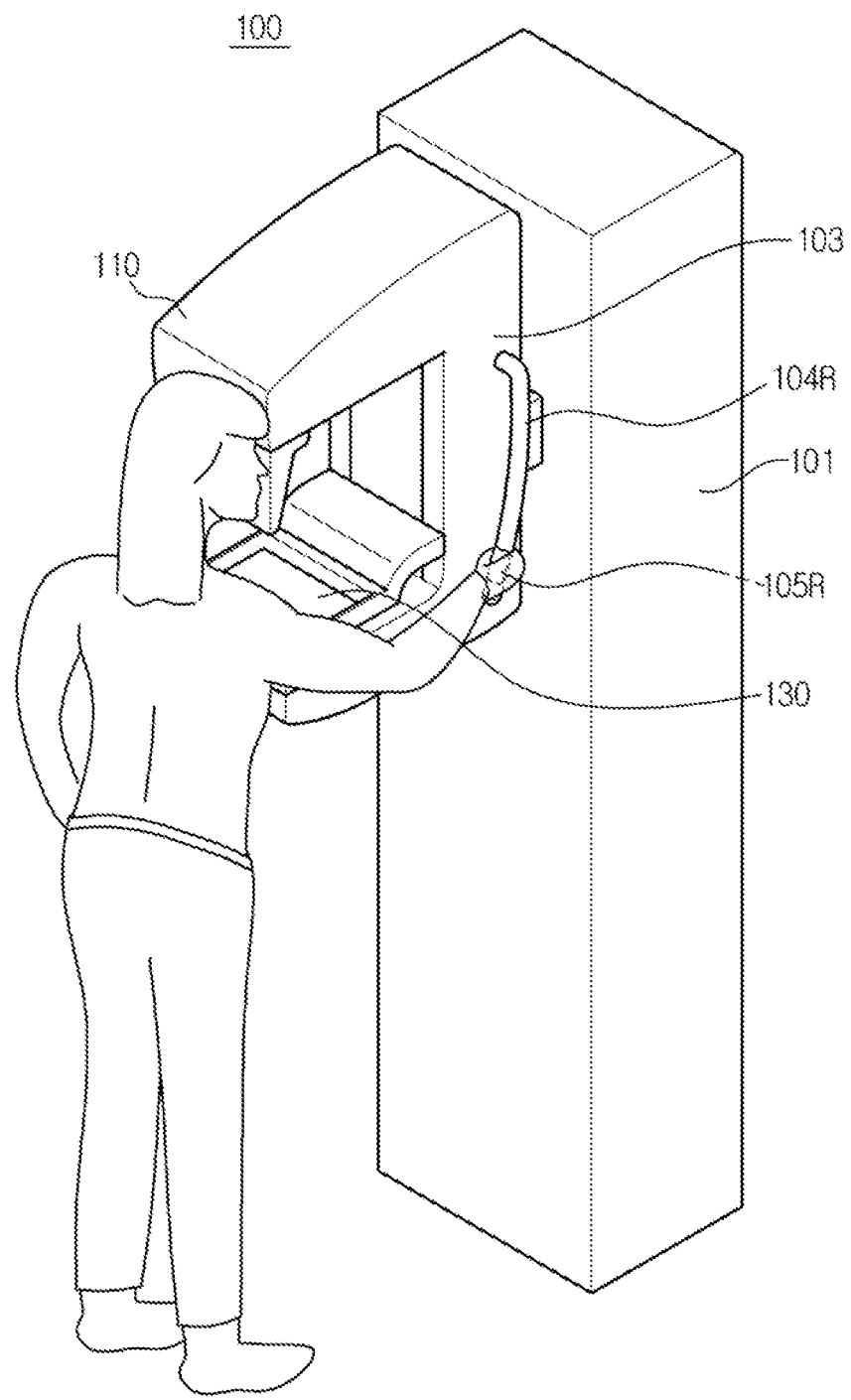
FIGS. 6A and 6B illustrate states when a patient keeps a grip on handles provided on an X-ray assembly upon mammography.
Figure 6B:
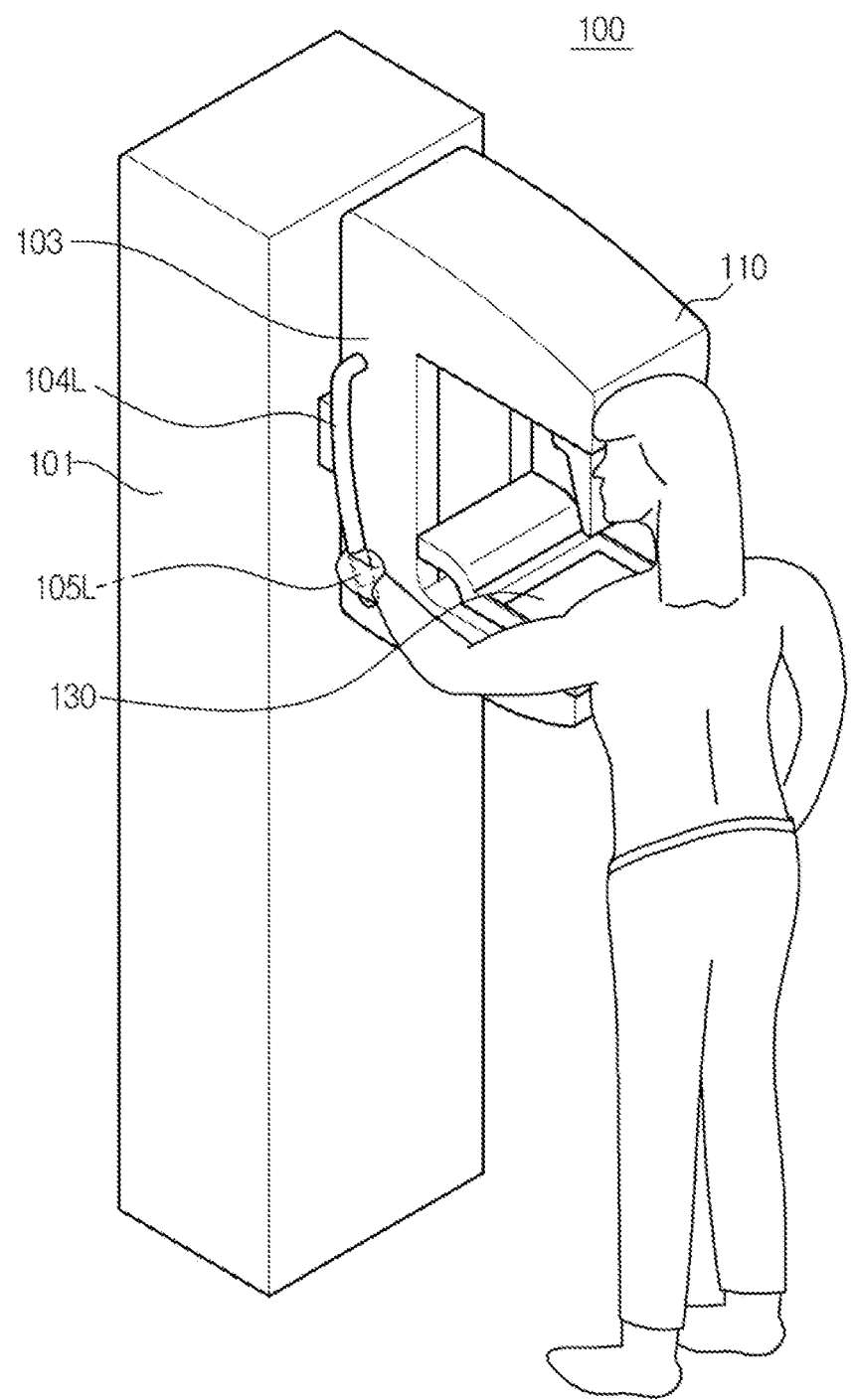

FIG. 4A is a block diagram of an X-ray imaging apparatus according to an exemplary embodiment, FIGS. 4B and 4C illustrate external appearances of an X-ray imaging apparatus according to an exemplary embodiment when the X-ray imaging apparatus is seen from the right side and when the X-ray imaging apparatus is seen from the left side, FIG. 5A illustrates an internal structure of an X-ray tube, FIG. 5B illustrates a structure of an X-ray detector, and FIGS. 6A and 6B illustrate states when a patient keeps a grip on handles provided on an X-ray assembly upon mammography.

Referring to FIGS. 4A to 4C, an X-ray imaging apparatus 100 includes an X-ray source 110 to generate X-rays and irradiate the X-rays onto an object, an X-ray detector 120 to detect X-rays transmitted through the object, and an X-ray assembly including a pressure paddle 130 to press the object placed on the X-ray detector 120. The X-ray source 110 is connected to the X-ray detector 120 by a frame 103, and the frame 103 is connected to a main body 101. In the current exemplary embodiment, the object is a region of an object, which is to be diagnosed by the X-ray imaging apparatus 100. Since the X-ray imaging apparatus 100 has been designed for mammography, the object is a breast.

The X-ray source 110 includes an X-ray tube 111 to generate X-rays, and the X-ray source 110 is also called an X-ray tube head or an X-ray tube assembly. Referring to FIG. 5A, the X-ray tube 111 may be embodied as a two-electrode vacuum tube including an anode 111$c$ and a cathode 111$e$, and the body of the two-electrode vacuum tube may be a glass tube 111$a$ made of silica (hard) glass or the like.

The cathode 111$e$ includes a filament 111$h$ and a focusing electrode 111$g$ for focusing electrons, and the focusing electrode 111$g$ is also called a focusing cup. The inside of a glass tube 111$a$ is evacuated to a high vacuum state of about 10 mmHg, and the filament 111$h$ of the cathode 111$e$ is heated to a high temperature, thereby generating thermo-electrons. The filament 111h may be a tungsten filament, and the filament 111h may be heated by applying current to electrical leads 111f connected to the filament 111h.

The anode 111c may be made of copper, and a target material 111d is applied on the surface of the anode 111c facing the cathode 111e, wherein the target material 111d may be a high-resistance material, e.g., Cr, Fe, Co, Ni, W, or Mo. The higher the melting point of the target material 111d, the smaller the focal spot size.

When a high voltage is applied between the cathode 111e and the anode 111c, thermoelectrons are accelerated and collide with the target material 111d of the anode 111e, thereby generating X-rays. The X-rays are irradiated to the outside through a window 111i. The window 111i may be a Beryllium (Be) thin film. Also, a filter (not shown) for filtering a specific energy band of X-rays may be provided on the front or rear side of the window 111i.

The target material 111d may be rotated by a rotor 111b. When the target material 111d rotates, the heat accumulation rate may increase 10 times per unit area and the focal spot size may be reduced, compared to when the target material 111d is fixed.

The voltage that is applied between the cathode 111e and the anode 111c of the X-ray tube 111 is called a tube voltage. The magnitude of a tube voltage may be expressed as a crest value (kVp). When the tube voltage increases, velocity of thermoelectrons increases accordingly. Then, energy (energy of photons) of X-rays that are generated when the thermoelectrons collide with the target material 111d also increases. Current flowing through the X-ray tube 111 is called tube current, and can be expressed as an average value (mA). When tube current increases, the number of thermoelectrons emitted from the filament 111h increases, and as a result, a dose of X-rays (that is, the number of X-ray photons) that are generated when the thermoelectrons collide with the target material 111d increases.

In summary, energy of X-rays can be controlled by adjusting a tube voltage. Also, a dose or intensities of X-rays can be controlled by adjusting tube current and an X-ray exposure time. Accordingly, it is possible to control energy or an intensity of X-rays that are to be irradiated to an object, according to the kind or properties of the object.

When X-rays to be irradiated have a predetermined energy band, the predetermined energy band may be defined by upper and lower limits. The upper limit of the predetermined energy band, that is, maximum energy of X-rays to be irradiated may be adjusted by the magnitude of a tube voltage, and the lower limit of the predetermined energy band, that is, minimum energy of X-rays to be irradiated may be adjusted by a filter. By filtering out a low energy band of X-rays using the filter, average energy of X-rays to be irradiated may increase.

Referring again to FIG. 4A, the controller 170 may set mammography conditions, such as, for example, a tube voltage, tube current, an X-ray exposure time, a filter type, a target material, a spot size, and an irradiation range of the X-ray tube 111. The controller 170 may automatically control the mammography conditions to perform Auto Exposure Control, or may control the mammography conditions according to a user's control command received through an input unit 181.

The X-ray detector 120 detects X-rays transmitted through an object. The X-ray detector 120 can be classified according to its configuration, a method of converting detected X-rays into electrical signals, and a method of acquiring image signals.

The X-ray detector 120 is classified into a mono type device or a hybrid type device according to its material configuration.

If the X-ray detector 120 is a mono type device, a part of detecting X-rays and generating electrical signals, and a part of reading and processing the electrical signals may be semiconductors made of the same material, or may be manufactured by one process. In this case, the X-ray detector 120 may be a Charge Coupled Device (CCD) or a Complementary Metal Oxide Semiconductor (CMOS) which is a light receiving device.

If the X-ray detector 120 is a hybrid type device, a part of detecting X-rays and generating electrical signals, and a part of reading and processing the electrical signals may be made of different materials, or may be manufactured by different processes. For example, there are cases of detecting X-rays using a photodiode or a light receiving device such as CdZnTe, and reading and processing electrical signals using a CMOS Read Out Integrated Circuit (CMOS ROIC), of detecting X-rays using a strip detector, and reading and processing electrical signals, and of using an amorphous silicon (a-Si) or amorphous selenium (a-Se) flat panel system.

The X-ray detector 120 may use a direct conversion mode and an indirect conversion mode according to a method of converting X-rays into electrical signals.

In the direct conversion mode, if X-rays are irradiated, electron-hole pairs are temporarily generated in a light receiving device, electrons move to an anode and holes move to a cathode by an electric field applied to both terminals of the light receiving device, and the X-ray detector 120 converts the movement of the electrons and holes into an electrical signal. The light receiving device may be made of a-Se, CdZnTe, $HgI_2$, or $PbI_2$.

In the indirect conversion mode, a scintillator is provided between a light receiving device and an X-ray source. If X-rays irradiated from an X-ray source react with the scintillator to emit photons having a wavelength of a visible light region, the light receiving device detects the photons, and converts the photons into an electrical signal. The light receiving device may be made of a-Si, and the scintillator may be a GADOX scintillator of a thin film type, or a CSI (TI) of a micro pillar type or a needle type.

The X-ray detector 120 may use a charge integration mode of storing charges for a predetermined time period and then acquiring a signal from the stored charges, or a photon counting mode of counting the number of photons having energy higher than threshold energy whenever a signal is generated by single X-ray photons, according to a method of acquiring image signals.

The material configuration of the X-ray detector 120 and the signal conversion method of the X-ray detector 120 are not limited, however, for convenience of description, in an exemplary embodiment which will be described below, the X-ray detector 120 uses the direct conversion mode of acquiring electrical signals directly from X-rays, and the X-ray detector 120 is a hybrid type in which a light receiving device for detecting X-rays is integrated with a read circuit chip.

Referring to FIG. 5B, an X-ray detector 120 includes a light receiving device 140 to detect X-rays and convert the X-rays into electrical signals, and a read circuit 146 to read out the electrical signals. The read circuit 146 includes a two-dimensional (2D) pixel array including a plurality of pixel areas. The light receiving device 140 may be made of a single crystal semiconductor material in order to ensure high resolution, high response speed, and a high dynamic area even under conditions of low energy and a small dose of X-rays. The single crystal semiconductor material may be Ge, CdTe, CdZnTe, or GaAs.

The light receiving device 140 may be in the form of a PIN photodiode. The PIN photodiode is fabricated by bonding a p-type layer 142 in which p-type semiconductors are arranged in the form of a 2D pixel array on the lower surface of a n-type semiconductor substrate 144 having high resistance. The read circuit 121-2, which is fabricated according to a CMOS process, is coupled with the light receiving device 140 in units of pixels. The CMOS read circuit 146 and the light receiving device 140 may be coupled by a Flip-Chip Bonding (FCB) method. More specifically, the CMOS read circuit 146 and the light receiving device 140 may be coupled by forming bumps 148 with PbSn, In, or the like, reflowing, applying heat, and then compressing. However, the X-ray detector 120 is not limited to this structure.

Referring to FIGS. 4B and 4C, if an object is positioned on the X-ray detector 120 for mammography, the pressure paddle 130 which is movable in an up-down direction along the frame 103 presses the object to adjust the thickness of the object to a thickness suitable for mammography. The pressure paddle 130 may be moved manually by a user, or may move automatically according to a predetermined value. If the pressure paddle 130 moves automatically, the controller 170 transmits a control signal to a paddle driver for driving the pressure paddle 130 in order to move the pressure paddle 130. The paddle driver may include a motor to provide power to the pressure paddle 130. Movement of the pressure paddle 130 may be automatically adjusted according to a predetermined value or according to the properties of the object. For example, if an object thickness required for mammography has been set to 5 cm, the controller 170 transmits a control signal to the paddle driver so as for the paddle driver to move the pressure paddle 130 to a location spaced by 5 cm apart from the X-ray detector 120.

In the current exemplary embodiment, the user is a person who diagnoses an object using the X-ray imaging apparatus 100, and the user may be a medical staff including a doctor, a radiologist, and a nurse. However, the user is not limited to a medical staff, and may be anyone using the X-ray imaging apparatus 100.

Referring to FIGS. 4B and 4C, handles 104R and 104L which a patient can grip upon mammography are respectively provided in the right and left sides of the X-ray assembly. In detail, the handles 104R and 104L are respectively provided in the right and left sides of the X-ray assembly based on a direction in which a patent's front side faces upon mammography, that is, a direction in which the patient looks upon mammography.

A patient can hold a more stable pose during mammography by gripping the handles 104R and 104L. An operator can induce the patient to grip a handle 104R or 104L located close to a breast on which mammography is performed so that mammography can be performed under the patient's stable pose.

Each of the handles 104R and 104L may have an arbitrary shape which a patient can grip, and the shapes or structures of the handles 104R and 104L are not limited.

The handles 104R and 104L include first sensors 105 for detecting a patient's grip. The first sensors 105 are respectively installed in the handles 104R and 104L provided in the right and left sides of the X-ray assembly.

Although locations at which the first sensors 105 are installed in the handles 104R and 104L are not limited, the first sensors 105 may include a first right sensor 105R and a first left sensor 105L installed at corresponding portions of the handles 104R and 104L at which the patient can easily grip. Also, the operator may induce the patient to grip the portions of the handles 104R and 104L at which the first sensors 105 are installed.

The first sensors 105 may be tactile sensors or proximity sensors capable of detecting a patient's grip on the handles 104R and 104L in which the first sensors 105 are installed. Also, the first sensors 105 may be embodied as mechanical buttons or capacitive buttons. However, the first sensors 105 are not limited to the above examples, and may be any other type sensors capable of detecting a patient's grip.

If a patient grips the portions of the handles 104R and 104L at which the first sensors 105 are installed, the first sensors 105 detect the patient's grip, convert the patient's grip into electrical signals, and then transmit the electrical signals to the controller 170 (see FIG. 4A). For example, as illustrated in FIG. 6A, if a patient grips the right handle 104R, the first right sensor 105R installed in the right handle 104R outputs a signal to the controller 170, and the controller 170 determines that the patient has gripped the right handle 104R with her right hand. In contrast, as illustrated in FIG. 6B, if a patient grips the left handle 104L, the first left sensor 105L installed in the left handle 104L outputs a signal to the controller 170, and the controller 170 determines that the patient has gripped the left handle 104L with her left hand.

Generally, upon mammography of a right breast, a patient grips the right handle 104R with her right hand, and upon mammography of a left breast, a patient grips the left handle 104L with her left hand. This may be induced by an operator. That is, the left/right position of a breast being subject to mammography is identical to the left/right position of the handle which the patient grips.

Accordingly, the controller 170 can determine a left/right position of a breast being subject to mammography, based on which one of the first sensors 105 installed in the handles 104R and 104L outputs a signal.

As illustrated in FIG. 6A, if a patient grips the right handle 104R for mammography of her right breast, the first right sensor 105R installed in the right handle 104R detects the right hand's grip, converts the right hand's grip into an electrical signal, and outputs the electrical signal to the controller 170. If the controller 170 receives the signal output from the first right sensor 105R, the controller 170 determines that a breast being subject to mammography is the patient's right breast.

In contrast, as illustrated in FIG. 6B, if a patient grips the left handle 104L for mammography of her left breast, the first left sensor 105L installed in the left handle 104L detects the left hand's grip, converts the left hand's grip into an electrical signal, and outputs the electrical signal to the controller 170. If the controller 170 receives the signal output from the first left sensor 105L, the controller 170 determines that a breast being subject to mammography is the patient's left breast.

After the controller 170 determines a left/right position of a breast being subject to mammography, the controller 170 stores information regarding the left/right position of the breast in the patient's diagnosis record, thus preventing an error which may be generated when an operator records information regarding a left/right position of a breast being subject to mammography. Also, when an operator inputs information regarding a left/right position of a breast, the operator may refer to the information stored in the patient's diagnosis record as ancillary information. In addition, if an input from the operator is not identical to information stored by the controller 170, the controller 170 may output a warning message so as for the operator to again check a left/right position of a breast being subject to mammography.

Figure 7A:
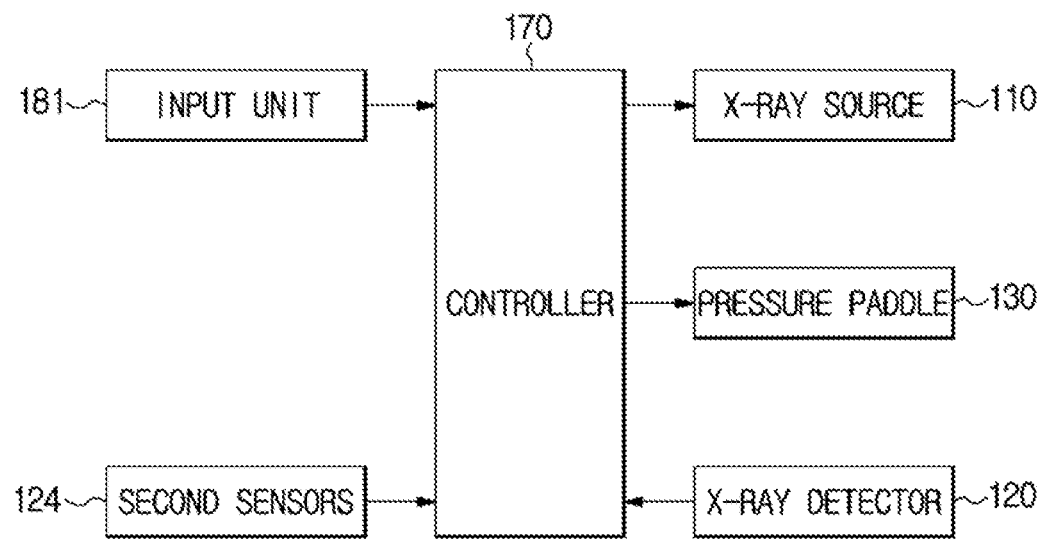
FIG. 7A is a block diagram of an X-ray imaging apparatus according to an exemplary embodiment.
Figure 7B:
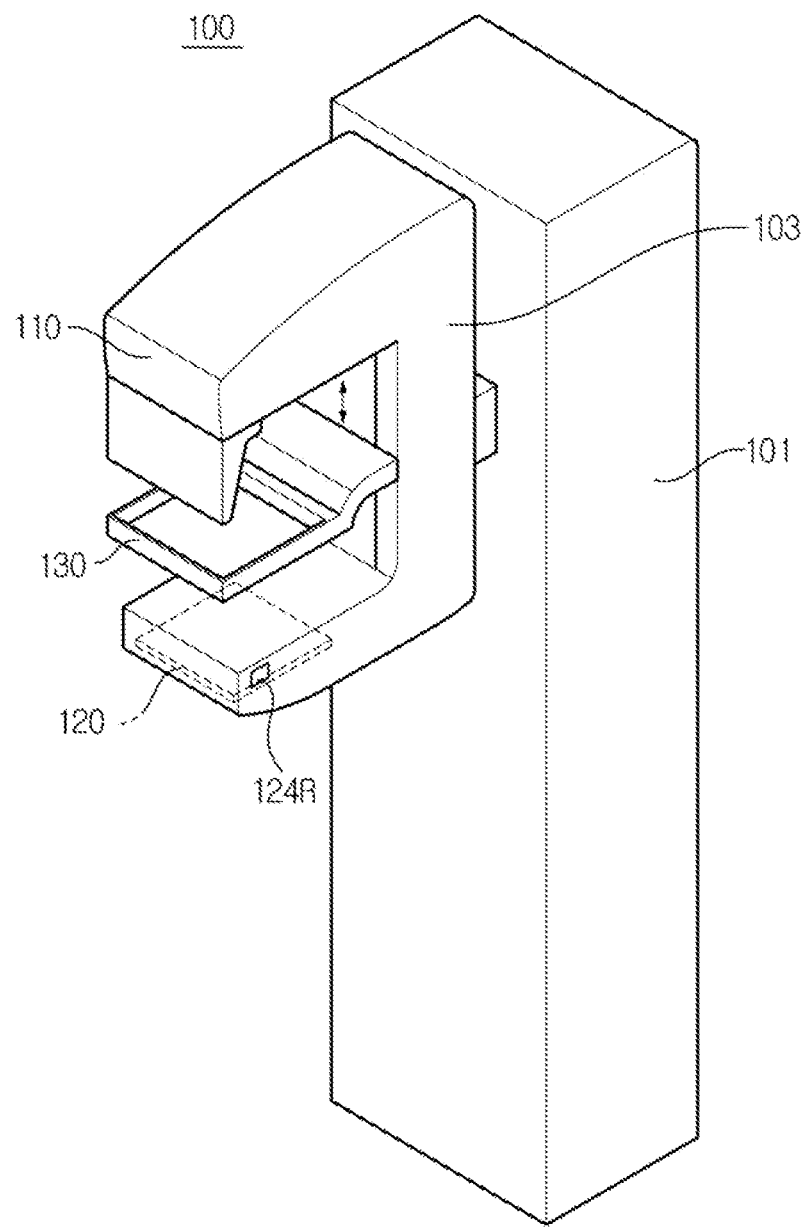
FIGS. 7B and 7C illustrate an X-ray imaging apparatus according to an exemplary embodiment when the X-ray imaging apparatus is seen from the right side and when the X-ray imaging apparatus is seen from the left side.
Figure 7C:
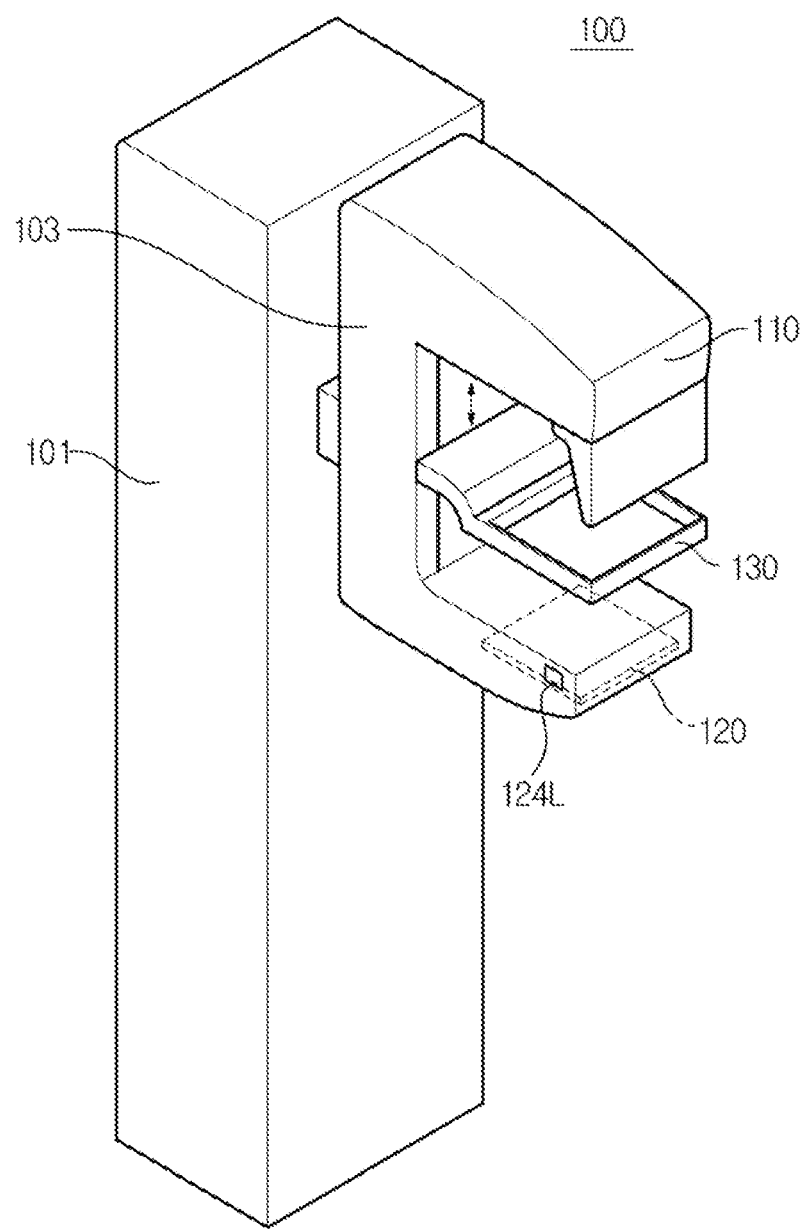
Figure 8A:
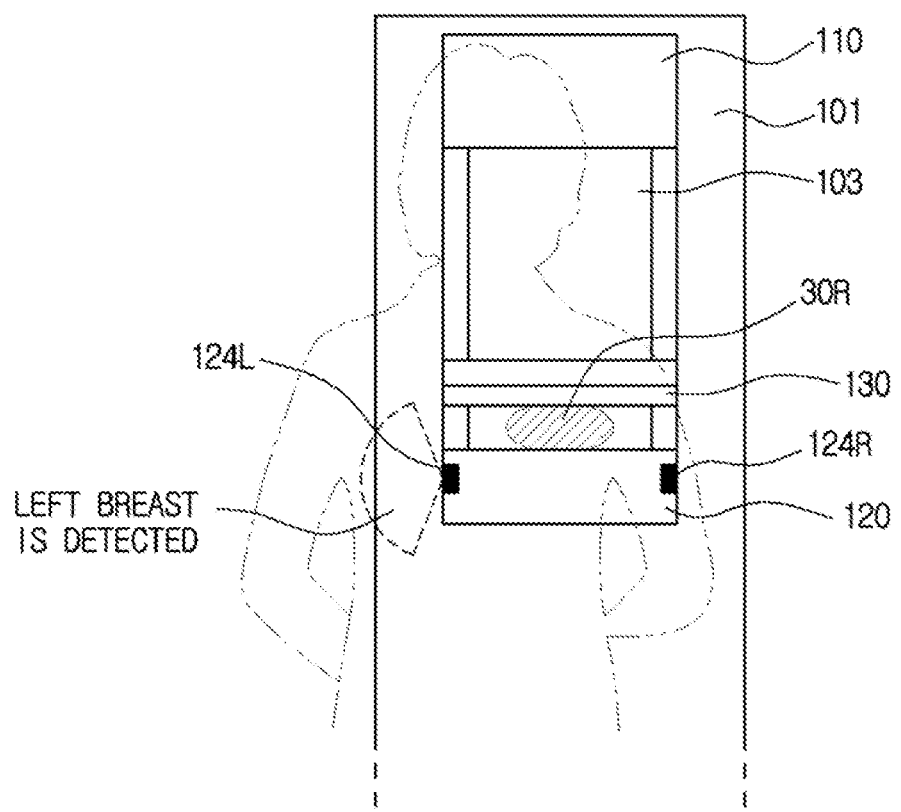
FIGS. 8A and 8B illustrate states when breasts are sensed by sensors installed in an X-ray detector.
Figure 8B:
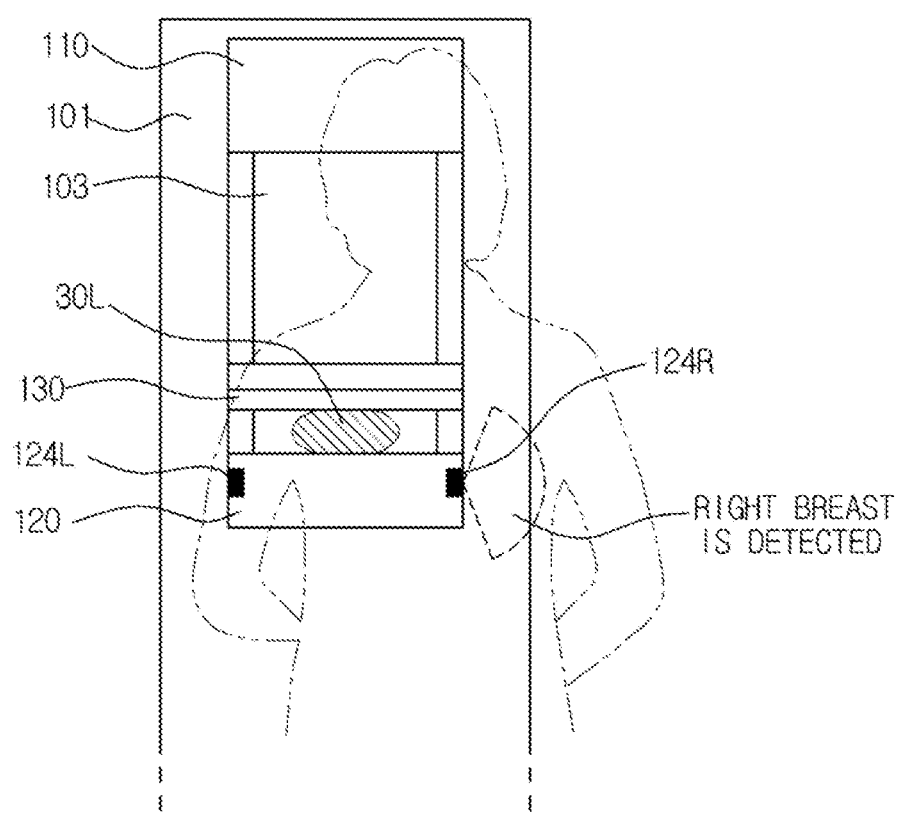

FIG. 7A is a block diagram of an X-ray imaging apparatus according to an exemplary embodiment, FIGS. 7B and 7C illustrate external appearances of an X-ray imaging apparatus according to an exemplary embodiment when the X-ray imaging apparatus is seen from the right side and when the X-ray imaging apparatus is seen from the left side, and FIGS. 8A and 8B illustrate states when breasts are sensed by sensors installed in an X-ray detector.

Referring to FIGS. 7A to 7C, the X-ray imaging apparatus according to an exemplary embodiment includes an X-ray source 110 to generate X-rays and irradiate the X-rays onto an object, an X-ray detector 120 to detect X-rays transmitted through the object, and an X-ray assembly including a pressure paddle 130 to press the object placed on the X-ray detector 120. The X-ray source 110 is connected to the X-ray detector 120 by a frame 103, and the frame 103 is connected to a main body 101. The X-ray source 110, the X-ray detector 120, and the pressure paddle 130 have been described in the above-described exemplary embodiments, and accordingly, further descriptions thereof will be omitted.

Second sensors 124 for detecting breasts are respectively installed in the right and left sides of the X-ray detector 120. The second sensors 124 may be respectively installed in the right and left sides of the X-ray detector 120, based on a direction in which a patent's front side faces upon mammography, that is, a direction in which the patient looks upon mammography. FIG. 7B shows the second right sensor 124R installed in the right side of the X-ray detector 120, and FIG. 7C shows the second left sensor 124L installed in the left side of the X-ray detector 120. The number or locations of the second sensors illustrated in FIGS. 7B and 7C are only exemplary, and one or more sensors may be installed in each side of the X-ray detector 120, or the sensors may be installed at different locations in the right and left sides of the X-ray detector 120.

The second sensors 124 may be provided to detect breasts placed close to the second sensors 124 upon mammography. The second sensors 124 may be proximity sensors. However, the second sensors 124 are not limited to proximity sensors, and may be any other type sensors capable of detecting breasts placed close to the second sensors 124. For example, the second sensors 124 may acquire images of breasts placed close to the second sensors 124 using cameras.

The controller 170 (see FIG. 7A) determines a left/right position of a breast being subject to mammography, based on signals detected by the second sensors 124.

Referring to FIG. 8A, upon mammography of a patient's right breast 30R, the second left sensor 124L installed in the left side of the X-ray detector 120 may detect the left breast 30L which is not subject to mammography. However, the second right sensor 124R installed in the right side of the X-ray detector 120 cannot detect the right breast 30R being subject to mammography, or may weakly detect the right breast 30R depending on a sensing range of the second right sensor 124R.

Since the second left sensor 124L installed in the left side of the X-ray detector 120 senses the left breast 30L over the entire sensing range, the second left sensor 124L outputs a signal with a greater magnitude than the second right sensor 124R installed in the right side of the X-ray detector 120.

The controller 170 receives the signals output from the second sensors 124, determines a position of the second left sensor 124L that has output the signal with the greater magnitude, and determines a breast corresponding to an opposite position of the determined position, as a breast being subject to mammography. As described above, upon mammography of the right breast 30R, since a signal output from the second left sensor 124L installed in the left side of the X-ray detector 120 has a greater magnitude, the controller 170 determines the right breast 30R corresponding to an opposite position to that of the second left sensor 124L that has output the signal with the greater magnitude, as a breast being subject to mammography.

Referring to FIG. 8B, upon mammography of a patient's left breast 30L, the second right sensor 124R installed in the right side of the X-ray detector 120 may detect the right breast 30R which is not subject to mammography. However, the second left sensor 124L installed in the left side of the X-ray detector 120 cannot detect the left breast 30L being subject to mammography, or may weakly detect the left breast 30L depending on a sensing range of the second left sensor 124L.

Since the second right sensor 124R installed in the right side of the X-ray detector 120 senses the right breast 30R over the entire sensing range, the second right sensor 124R outputs a signal with a greater magnitude than the second left sensor 124L installed in the left side of the X-ray detector 120.

The controller 170 receives the signals output from the second sensors 124, determines a position of the second right sensor 124R that has output the signal with the greater magnitude, and determines a breast corresponding to an opposite position of the determined position, as a breast being subject to mammography. As described above, upon mammography of the left breast 30L, since a signal output from the second right sensor 124R installed in the right side of the X-ray detector 120 has a greater magnitude, the controller 170 determines the left breast 30L corresponding to an opposite position to that of the second right sensor 124R that has output the signal with the greater magnitude, as a breast being subject to mammography.

After the controller 170 determines a left/right position of a breast being subject to mammography, the controller 170 stores information regarding the left/right position of the breast in the patient's diagnosis record, thus preventing an error which may be generated when an operator records information regarding a left/right position of a breast being subject to mammography. Also, when an operator inputs information regarding a left/right position of a breast, the operator may refer to the information stored in the patient's diagnosis record as ancillary information. In addition, if an input from the operator is not identical to information stored by the controller 170, the controller 170 may output a warning message so as for the operator to again check a left/right position of a breast being subject to mammography.

Figure 9A:
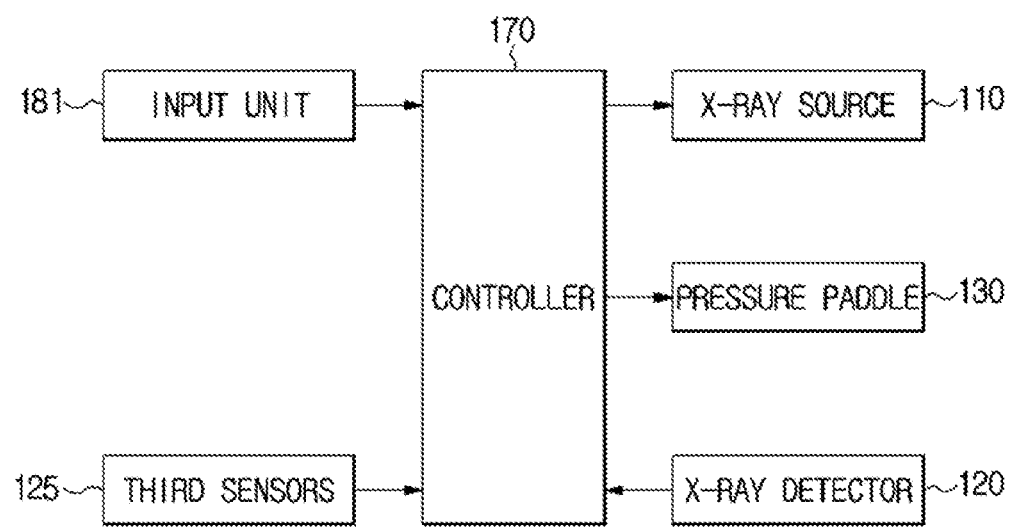
FIG. 9A is a block diagram of an X-ray imaging apparatus according to an exemplary embodiment.
Figure 9B:
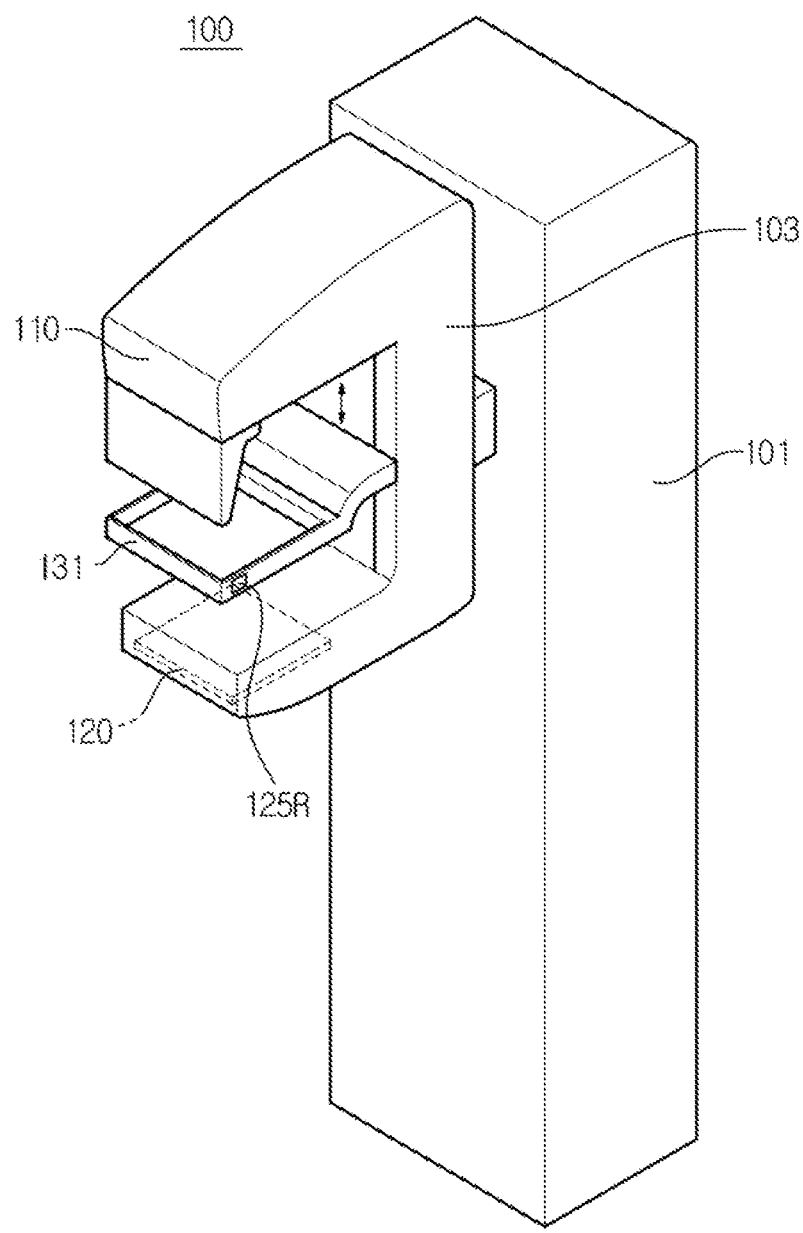
FIGS. 9B and 9C illustrate an X-ray imaging apparatus according to an exemplary embodiment when the X-ray imaging apparatus is seen from the right side and when the X-ray imaging apparatus is seen from the left side.
Figure 9C:
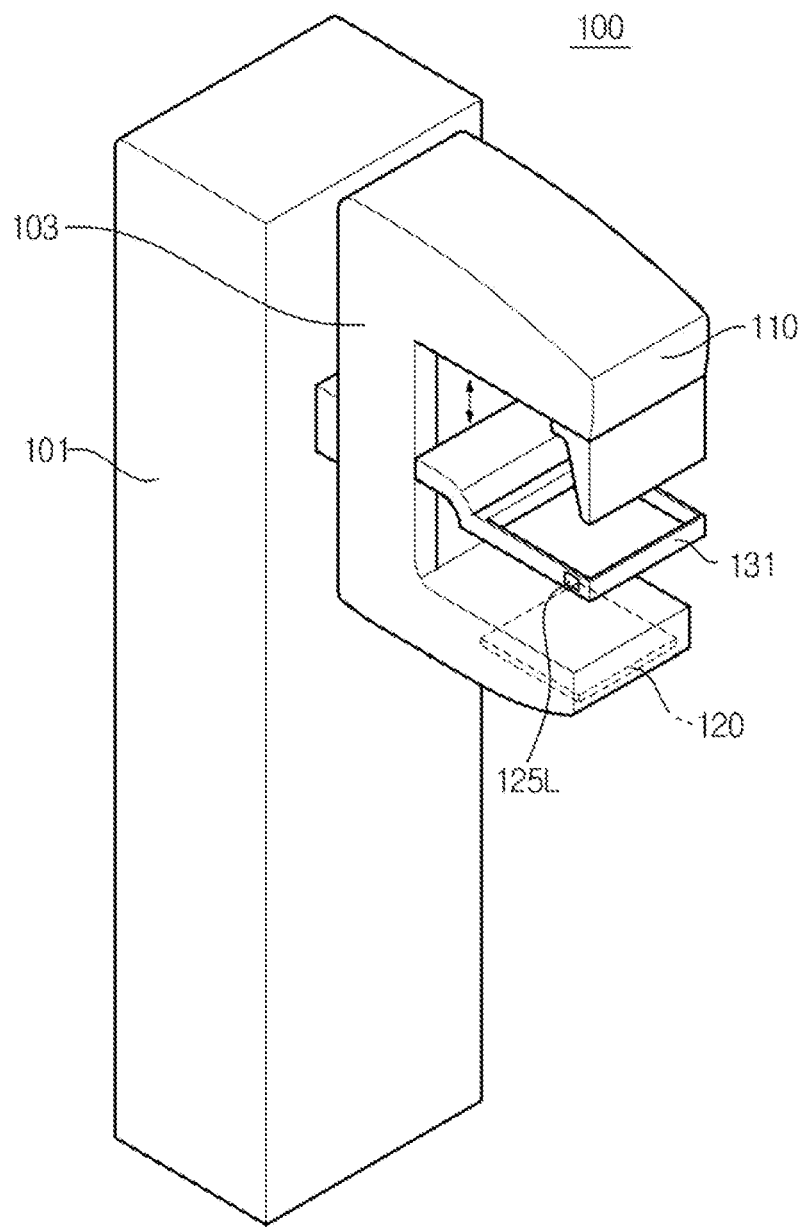
Figure 10A:
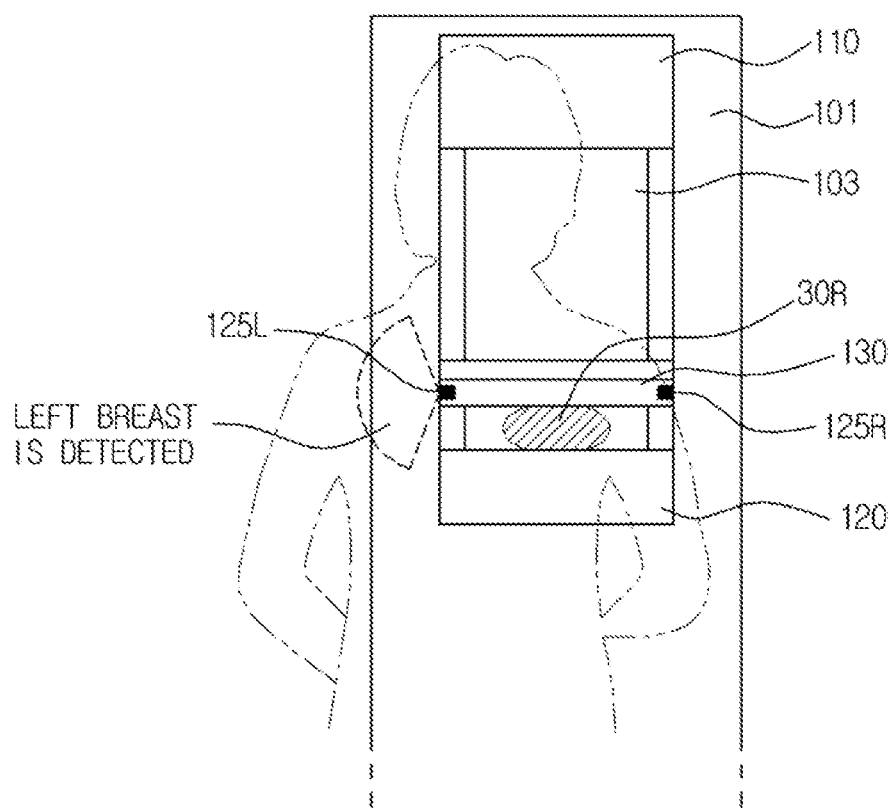
FIGS. 10A and 10B illustrate states when breasts are sensed by sensors.
Figure 10B:
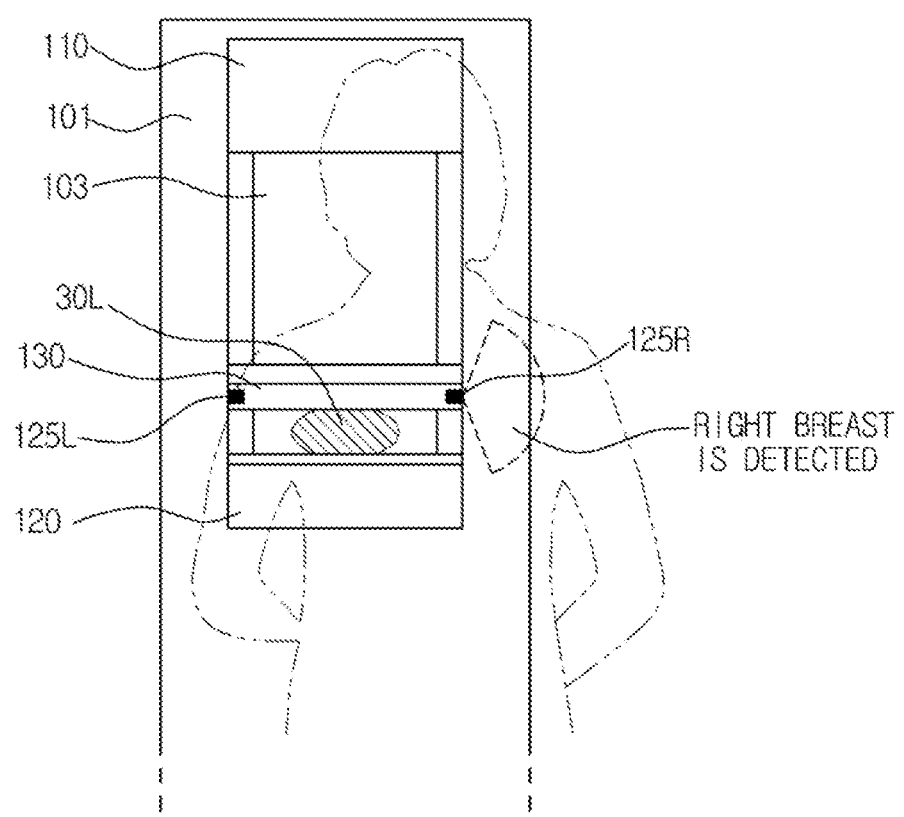

FIG. 9A is a block diagram of an X-ray imaging apparatus according to an exemplary embodiment, FIGS. 9B and 9C illustrate external appearances of an X-ray imaging apparatus according to an exemplary embodiment when the X-ray imaging apparatus is seen from the right side and when the X-ray imaging apparatus is seen from the left side, and FIGS. 10A and 10B illustrate states when breasts are sensed by sensors installed in the pressure paddle 130.

Referring to FIGS. 9A to 9C, the X-ray imaging apparatus according to an exemplary embodiment includes an X-ray source 110 to generate X-rays and irradiate the X-rays onto an object, an X-ray detector 120 to detect X-rays transmitted through the object, and an X-ray assembly including a pressure paddle 130 to press the object placed on the X-ray detector 120. The X-ray source 110 is connected to the X-ray detector 120 by a frame 103, and the frame 103 is connected to a main body 101. The X-ray source 110, the X-ray detector 120, and the pressure paddle 130 have been described in the above-described exemplary embodiments, and accordingly, further descriptions thereof will be omitted.

Third sensors 125 for detecting breasts placed close to the sensors are respectively installed in the right and left sides of the pressure paddle 130. The third sensors 125 may be respectively installed in the right and left sides of the pressure paddle 130, based on a direction in which a patent's front side faces upon mammography, that is, a direction in which the patient looks upon mammography.

FIG. 9B shows the third right sensor 125R installed in the right side of the pressure paddle 130, and FIG. 9C shows the third left sensor 125L installed in the left side of the pressure paddle 130. The number or locations of the sensors illustrated in FIGS. 9B and 9C are only exemplary, and one or more sensors may be installed in each side of the pressure paddle 130, or the sensors may be installed at different locations in the right and left sides of the pressure paddle 130.

The third sensors 125 may be provided to detect breasts placed close to the third sensors 125 upon mammography. The third sensors 125 may be proximity sensors. However, the third sensors 125 are not limited to proximity sensors, and may be any other type sensors capable of detecting breasts placed close to the sensors 125. For example, the third sensors 125 may acquire images of breasts placed close to the third sensors 125 using cameras.

The controller 170 (see FIG. 9A) determines a left/right position of a breast being subject to mammography, based on signals detected by the third sensors 125.

Referring to FIG. 10A, upon mammography of a patient's right breast 30R, the third left sensor 125L installed in the left side of the pressure paddle 130 may detect the left breast 30L which is not subject to mammography. However, the third right sensor 125R installed in the right side of the pressure paddle 130 cannot detect the right breast 30R being subject to mammography, or may weakly detect the right breast 30R depending on a sensing range of the third left sensor 125L.

Since the third left sensor 125L installed in the left side of the pressure paddle 130 senses the left breast 30L over the entire sensing range, the third left sensor 125L outputs a signal with a greater magnitude than the third right sensor 125R installed in the right side of the pressure paddle 130.

The controller 170 receives the signals output from the third sensors 125, determines a position of the third left sensor 125L that has output the signal with the greater magnitude, and determines a breast corresponding to an opposite position of the determined position, as a breast being subject to mammography. As described above, upon mammography of the right breast 30R, since a signal output from the third left sensor 125L installed in the left side of the pressure paddle 130 has a greater magnitude, the controller 170 determines the right breast 30R corresponding to an opposite position to that of the third left sensor 125L that has output the signal with the greater magnitude, as a breast being subject to mammography.

Referring to FIG. 10B, upon mammography of a patient's left breast 30L, the third right sensor 125R installed in the right side of the pressure paddle 130 may detect the right breast 30R which is not subject to mammography. However, the third left sensor 125L installed in the left side of the pressure paddle 130 cannot detect the left breast 30L being subject to mammography, or may weakly detect the left breast 30L depending on a sensing range of the third left sensor 125L.

Since the third right sensor 125R installed in the right side of the pressure paddle 130 senses the right breast 30R over the entire sensing range, the third right sensor 125R outputs a signal with a greater magnitude than the third left sensor 125L installed in the left side of the pressure paddle 130.

The controller 170 receives the signals output from the third sensors 125, determines a position of the third right sensor 125R that has output the signal with the greater magnitude, and determines a breast corresponding to an opposite position of the determined position, as a breast being subject to mammography. As described above, upon mammography of the left breast 30L, since a signal output from the third right sensor 125R installed in the right side of the pressure paddle 130 has a greater magnitude, the controller 170 determines the left breast 30L corresponding to an opposite position to that of the third right sensor 125R that has output the signal with the greater magnitude, as a breast being subject to mammography.

After the controller 170 determines a left/right position of a breast being subject to mammography, the controller 170 stores information regarding the left/right position of the breast in the patient's diagnosis record, thus preventing an error which may be generated when an operator records information regarding a left/right position of a breast being subject to mammography. Also, when an operator inputs information regarding a left/right position of a breast, the operator may refer to the information stored in the patient's diagnosis record as ancillary information. In addition, if an input from the operator is not identical to information stored by the controller 170, the controller 170 may output a warning message so as for the operator to again check a left/right position of a breast being subject to mammography.

As described above, the controller 170 determines a breast being subject to mammography, based on signals output from at least one of the first sensors 105, the second sensors 124, and the third sensors 125.

Alternatively, the controller 170 may determine a candidate of a breast being subject to mammography, based on signals output from the first sensors 105, and determines the candidate of the breast being subject to mammography, as a breast being subject to mammography, based on signals output from the second sensors 124 or from the third sensors 125. The second sensors 124 and the third sensors 125 are used to determine a breast being subject to mammography in the same way or in a different way and the second sensors 124 and the third sensors 125 may be disposed at different locations.

Hereinafter, a method of determining a candidate of a breast being subject to mammography based on signals output from the first sensors 105 and signals output from at least one of the second sensors 124 and the third sensors 125 will be described in detail.

The controller 170 determines a candidate of a breast being subject to mammography based on signals output from the first sensors 105.

If a patient grips one of portions of the handles 104R and 104L (see FIGS. 4B and 4C) at which the first sensors 105 are installed, at least one of the first right sensor 105R or the first left sensor 105L senses the patient's grip, converts the patient's grip into an electrical signal, and transmits the electrical signal to the controller 170.

Accordingly, the controller 170 may determine a left/right position of a breast being subject to mammography, based on which one of the first sensors 105 installed in the right and left handles 104R and 104L outputs a signal.

The controller 170 may further determine a candidate of a breast being subject to mammography, as a breast being subject to mammography, based on signals output from the second sensors 124 or the third sensors 125, as described above. For example, the controller 170 may verify the result provided by the signals output by the first sensors 105 if both first sensors 105 provide a signal or if the provided signal is noisy, etc.

As such, by determining a breast being subject to mammography using all or some of the signals output from the first sensors 105, the second sensors 124, and/or the third sensors, a breast being subject to mammography can be determined with high reliability, thus obviating a need for further X-rays.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. An X-ray imaging apparatus for mammography, the apparatus comprising:
    an X-ray assembly configured to press a breast, to irradiate X-rays onto the pressed breast, and to detect X-rays transmitted through the breast;
    at least two handles, each of the two handles being provided in each of both sides of the X-ray assembly so that a patient is able to grip at least one of the two handles, and respectively including a sensor configured to detect a patient's grip; and
    a controller configured to determine a position of a handle which includes a respective sensor that has detected the patient's grip, and to determine that a breast subject to the mammography is a breast corresponding to the determined position.

2. The X-ray imaging apparatus according to claim 1, wherein each of the two handles is respectively provided in a right side and a left side of the X-ray assembly based on a direction in which a patient's front side faces during the mammography, and
    positions of the sensors included in each handle is determined to be the same position as an installation position of the handle on the X-ray assembly.

3. The X-ray imaging apparatus according to claim 2, wherein the controller determines that the breast subject to the mammography is a right breast when a detection signal is output from the sensor included in the handle provided in the right side of the X-assembly, and
    the controller determines that the breast subject to the mammography is a left breast when the detection signal is output from the sensor included in the handle provided in the left side of the X-ray assembly.

4. The X-ray imaging apparatus according to claim 1, wherein the sensors include at least one of a tactile sensor, a mechanical sensor, a capacitive sensor, and a proximity sensor.

5. The X-ray imaging apparatus according to claim 1, wherein the X-ray assembly comprises:
    an X-ray source configured to irradiate the X-rays onto the breast;
    an X-ray detector configured to detect the X-rays transmitted through the breast; and
    a pressure paddle configured to press the breast placed on the X-ray detector.

6. An X-ray imaging apparatus for mammography, the apparatus comprising:
    an X-ray source;
    an X-ray detector;
    a pressure paddle configured to press a breast placed on the X-ray detector;
    at least two sensors installed at least in one of the X-ray detector and the pressure paddle, and configured to detect breasts placed in close proximity to the sensors; and
    a controller configured to determine that a breast subject to the mammography is an opposite breast of the breast detected by a corresponding sensor.

7. The X-ray imaging apparatus according to claim 6, wherein each of the two sensors is respectively installed in each of both sides of the X-ray detector, and
    positions of the two sensors are respectively determined to be right and left positions based on a direction in which a patient's front side faces during the mammography.

8. The X-ray imaging apparatus according to claim 7, wherein the controller is configured to receive detection signals output from the two sensors installed in the both sides of the X-ray detector,
    determine a position of the corresponding sensor that has output a detection signal with a greater magnitude, from the received detection signals, and
    determine that the breast subject to the mammography is a breast corresponding to an opposite position of the determined position of the corresponding sensor that has output the detection signal with the greater magnitude.

9. The X-ray imaging apparatus according to claim 7, wherein the controller determines that the breast subject to the mammography is a left breast when a detection signal output from the sensor installed in a right side of the X-ray detector has a greater magnitude than that of a detection signal output from the sensor installed in a left side of the X-ray detector, and
    the controller determines that the breast subject to the mammography is a right breast when the detection signal output from the sensor installed in the left side of the X-ray detector has the greater magnitude than that of the detection signal output from the sensor installed in the right side of the X-ray detector.

10. The X-ray imaging apparatus according to claim 6, wherein each of the two sensors is respectively installed in each of both sides of the pressure paddle, and
    positions of the two sensors are respectively determined to be right and left positions based on a direction in which a patient's front side faces during the mammography.

11. The X-ray imaging apparatus according to claim 10, wherein the controller is configured to receive detection signals output from respective sensors installed in the both sides of the pressure paddle, determine a position of the sensor that has output a detection signal with a greater magnitude, from the received detection signals, and determine that the breast subject to the mammography is a breast corresponding to an opposite position of the determined position of the sensor that has output the detection signal with the greater magnitude.

12. The X-ray imaging apparatus according to claim 10, wherein the controller determines that the breast subject to the mammography is a left breast when a detection signal output from the sensor installed in a right side of the pressure paddle has a greater magnitude than that of the detection signal output from the sensor installed in a left side of the pressure paddle, and the controller determines that the breast subject to the mammography is a right breast when the detection signal output from the sensor installed in the left side of the pressure paddle has the greater magnitude than that of the detection signal output from the sensor installed in the right side of the pressure paddle.

13. The X-ray imaging apparatus of claim 7, wherein the two sensors include at least one of a proximity sensor, an image sensor, and a camera.

14. An X-ray imaging apparatus for mammography, the apparatus comprising:
an X-ray assembly including an X-ray source, an X-ray detector, and a pressure paddle configured to press a breast placed on the X-ray detector;
at least two handles, each of the two handles being provided in each of both sides of the X-ray assembly so that a patient is able to grip at least one of the handles, and including a first sensor configured to detect a patient's grip; and
at least two second sensors installed at least in one of the X-ray detector and the pressure paddle, and configured to detect breasts placed in close proximity to the second sensors; and
a controller configured to determine whether a breast subject to the mammography is a left breast or a right breast, based on detection signals output from at least one of the first sensors and the second sensors.

15. The X-ray imaging apparatus according to claim 14, wherein the controller determines a breast corresponding to the same position as that of a handle including a respective first sensor that has detected the patient's grip and output a detection signal, as a candidate breast subject to the mammography;
the controller determines whether a breast corresponding to an opposite position of that of a respective second sensor that has output a detection signal with a greater magnitude between the detection signals output from the second sensors is identical to the candidate breast determined based on the detection signal output from the respective first sensor; and
the controller determines the candidate breast determined based on the detection signal output from the respective first sensor as the breast subject to the mammography, when the breast corresponding to the opposite position of that of the respective second sensor that has output the detection signal with the greater magnitude is identical to the candidate breast.

16. The X-ray imaging apparatus according to claim 14, wherein the controller determines a breast corresponding to an opposite position of that of a respective second sensor that has output a detection signal with a greater magnitude between the detection signals output from the two second sensors, as a candidate breast subject to the mammography;

when a detection signal is output from one of the first sensors, the controller determines whether a breast corresponding to the same position as that of a handle including a respective first sensor that has output the detection signal is identical to the candidate breast; and the controller determines the candidate breast as the breast subject to the mammography when the breast having the same position as that of the handle including the respective first sensor that has output the detection signal is identical to the candidate breast.

17. The X-ray imaging apparatus according to claim 14, wherein each of the two handles is provided in a right side and a left side of the X-ray assembly based on a direction in which a patient's front side faces during the mammography, and a position of the first sensor included in each of the two handles is determined to be the same position as an installation position of the handle on the X-ray assembly.

18. The X-ray imaging apparatus according to claim 14, wherein each of the two second sensors is installed in each of both sides of the X-ray detector, and positions of the two second sensors are respectively determined to be right and left positions based on a direction in which a patient's front side faces during the mammography.

19. The X-ray imaging apparatus according to claim 14, wherein each of the two second sensors is installed in each of both sides of the pressure paddle, and positions of the two second sensors are respectively determined to be right and left positions based on a direction in which a patient's front side faces during the mammography.

* * * * *